US009372330B2

(12) United States Patent  
Amano et al.

(10) Patent No.: US 9,372,330 B2  
(45) Date of Patent: Jun. 21, 2016

(54) INVERTED MICROSCOPE SYSTEM

(71) Applicant: OLYMPUS CORPORATION, Shibuya-ku, Tokyo (JP)

(72) Inventors: Yusuke Amano, Hachioji (JP); Masayoshi Karasawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 111 days.

(21) Appl. No.: 14/226,537

(22) Filed: Mar. 26, 2014

(65) Prior Publication Data

US 2014/0293407 A1  Oct. 2, 2014

(30) Foreign Application Priority Data

Mar. 29, 2013  (JP) .................. 2013-072213

(51) Int. Cl.
*G02B 21/00* (2006.01)
*G01N 21/64* (2006.01)

(52) U.S. Cl.
CPC .......... *G02B 21/0044* (2013.01); *G01N 21/648* (2013.01); *G02B 21/0076* (2013.01); *G02B 21/0088* (2013.01)

(58) Field of Classification Search
CPC .. G02B 21/00; G02B 21/002; G02B 21/0024; G02B 21/0036; G02B 21/0044; G02B 21/0076; G02B 21/0088; G02B 21/16; G01N 21/6428; G01N 21/6447; G01N 21/6458; G01N 21/648
See application file for complete search history.

(56) References Cited

U.S. PATENT DOCUMENTS 4,336,997 A * 6/1982 Ross ................ G01S 17/08
250/201.4
5,825,533 A * 10/1998 Yonezawa .......... G02B 21/0044
359/372

(Continued)

FOREIGN PATENT DOCUMENTS

JP  2005-024647 A  1/2005

OTHER PUBLICATIONS

"Nikon Spinning-disk Confocal Microscope with TIRF Module," The David H. Koch Institute for Integrative Cancer Research, http://ki.mit.edu/sbc/microscopy/instrumentation/spinning, available online at least as of Aug. 8, 2012 (per https://web.archive.org), accessed Sep. 2, 2015.*

*Primary Examiner* — Stephone B. Allen
*Assistant Examiner* — Adam W Booher
(74) *Attorney, Agent, or Firm* — Holtz, Holtz & Volek PC (57) ABSTRACT

An inverted microscope system includes an objective lens holding unit that holds an objective lens configured to collect at least observation light from a specimen, a tube lens configured to form an image using the observation light collected by the objective lens, a total internal reflection fluorescence microscopy optical system provided between the objective lens and the tube lens and configured to observe the observation light from the specimen using a total reflection illumination, and a disk scanning confocal optical system including a rotary disk on which a confocal opening is formed, the confocal opening being placed at a position substantially conjugate to a focus position of the objective lens. A relative distance between the focus position of the objective lens and the substantially conjugate position is changeable along an optical path of the observation light.

5 Claims, 9 Drawing Sheets

(56) References Cited

U.S. PATENT DOCUMENTS

| | | | |
|---|---|---|---|
| 5,847,867 A * | 12/1998 | Sugiyama | G02B 21/0044 359/235 |
| 2002/0097489 A1 * | 7/2002 | Kawano | G02B 21/16 359/388 |
| 2004/0262522 A1 * | 12/2004 | Kitahara | G02B 21/0048 250/341.8 |
| 2006/0124870 A1 * | 6/2006 | Bobanovic | G02B 21/0044 250/493.1 |

\* cited by examiner

INVERTED MICROSCOPE SYSTEM

CROSS-REFERENCE TO RELATED APPLICATIONS

This application is based upon and claims the benefit of priority from Japanese Patent Application No. 2013-072213, filed on Mar. 29, 2013, the entire contents of which are incorporated herein by reference.

BACKGROUND

1. Technical Field

The disclosure relates to an inverted microscope system that irradiates a specimen with illumination light to observe the specimen by receiving the light reflected from the specimen.

2. Related Art

A microscope that illuminates a specimen to observe the specimen has conventionally been used for observing, for example, a cell in the field of medicine, biology, or the like. Furthermore, in the industrial field, a microscope system is used for various purposes such as the quality management of a metal structure, the research development of new materials, or the inspection of electronic devices or magnetic heads.

Examples of an optical system used for observing fluorescence from a specimen include a total internal reflection fluorescence microscopy optical system. In the total internal reflection fluorescence microscopy optical system, illumination light is totally reflected from a glass interface on which a specimen is placed to illuminate only the specimen just near the glass interface using an evanescent wave generated by the total reflection illumination, and thus the generated fluorescence can be observed.

As an exemplary application of the total internal reflection fluorescence microscopy optical system, ion transfer from/into a cell membrane by light stimulation, for example, using channelrhodopsin attracts attention. A local light stimulation using channelrhodpsin can be performed in addition to the illumination observation of only the periphery of the cell membrane of the cell that sticks on the glass.

Here, there is a phenomenon in which channelrhodopsin changes the ionic concentration of the cell sticking on the glass and this puts the cell into an excitatory state, and then the excitation is propagated to cells around the cell. In that case, the cells around the cell exist on upper layers than the cell sticking on the glass from the glass surface. However, the observation range in the total internal reflection fluorescence microscopy optical system is up to several hundred nm from the glass interface within the reach of the evanescent wave. Thus, the phenomenon of the propagation cannot be observed in the total internal reflection fluorescence microscopy optical system.

On the other hand, there is a disk scanning confocal optical system as another optical system used for observing the fluorescence from a specimen. The disk scanning confocal optical system is capable of observing only the fluorescence from the specimen surface in real time by spinning, at a high speed, a disk on which a confocal opening such as a slit or a pinhole is placed at a position conjugate to the specimen surface (objective lens focal position).

In the disk scanning confocal optical system, the specimen is irradiated through the slit or pinhole on the disk and thus only a fluorescent image from a desirable cross-section can be observed in real time. In an observation, for example, of fluorescence resonance energy transfer (FRET), the excitation of the cell can be determined from the color of the fluorescence. Thus, even in an experimental system in which an excitatory state is propagated in the optical axis direction, the effect of sectioning that is a feature of the disk scanning confocal optical system makes it possible to detect the intensity of variations in the excitation state as color variations for each cross-section.

As a technique for performing a local light stimulation on a starting point of a propagation to observe the propagation of the excitatory state of a cell, for example, Japanese Laid-open Patent Publication No. 2005-24647 discloses a microscope that is a combination of a total internal reflection fluorescence microscopy optical system and a disk scanning confocal optical system. In the technique, the total internal reflection fluorescence microscopy optical system is placed below the specimen and the disk scanning confocal optical system is placed above the specimen.

SUMMARY

In some embodiments, an inverted microscope system includes an objective lens holding unit that holds an objective lens configured to collect at least observation light from a specimen, a tube lens configured to form an image using the observation light collected by the objective lens, a total internal reflection fluorescence microscopy optical system provided between the objective lens and the tube lens and configured to observe the observation light from the specimen using a total reflection illumination, and a disk scanning confocal optical system including a rotary disk on which a confocal opening is formed, the confocal opening being placed at a position substantially conjugate to a focus position of the objective lens. A relative distance between the focus position of the objective lens and the substantially conjugate position is changeable along an optical path of the observation light.

The above and other features, advantages and technical and industrial significance of this invention will be better understood by reading the following detailed description of embodiments of the invention, when considered in connection with the accompanying drawings.

DETAILED DESCRIPTION

Exemplary embodiments of the invention will be described below in detail with reference to the appended drawings. Note that the invention is not limited to the embodiments. Furthermore, each of the drawings to be referred to in the description merely schematically illustrates the shapes, sizes, and positional relationships of the components to the extent that the contents of the invention can be understood. In other words, the invention is not limited to the shapes, sizes, and positional relationships illustrated as examples in each of the drawings.

Figure 1:
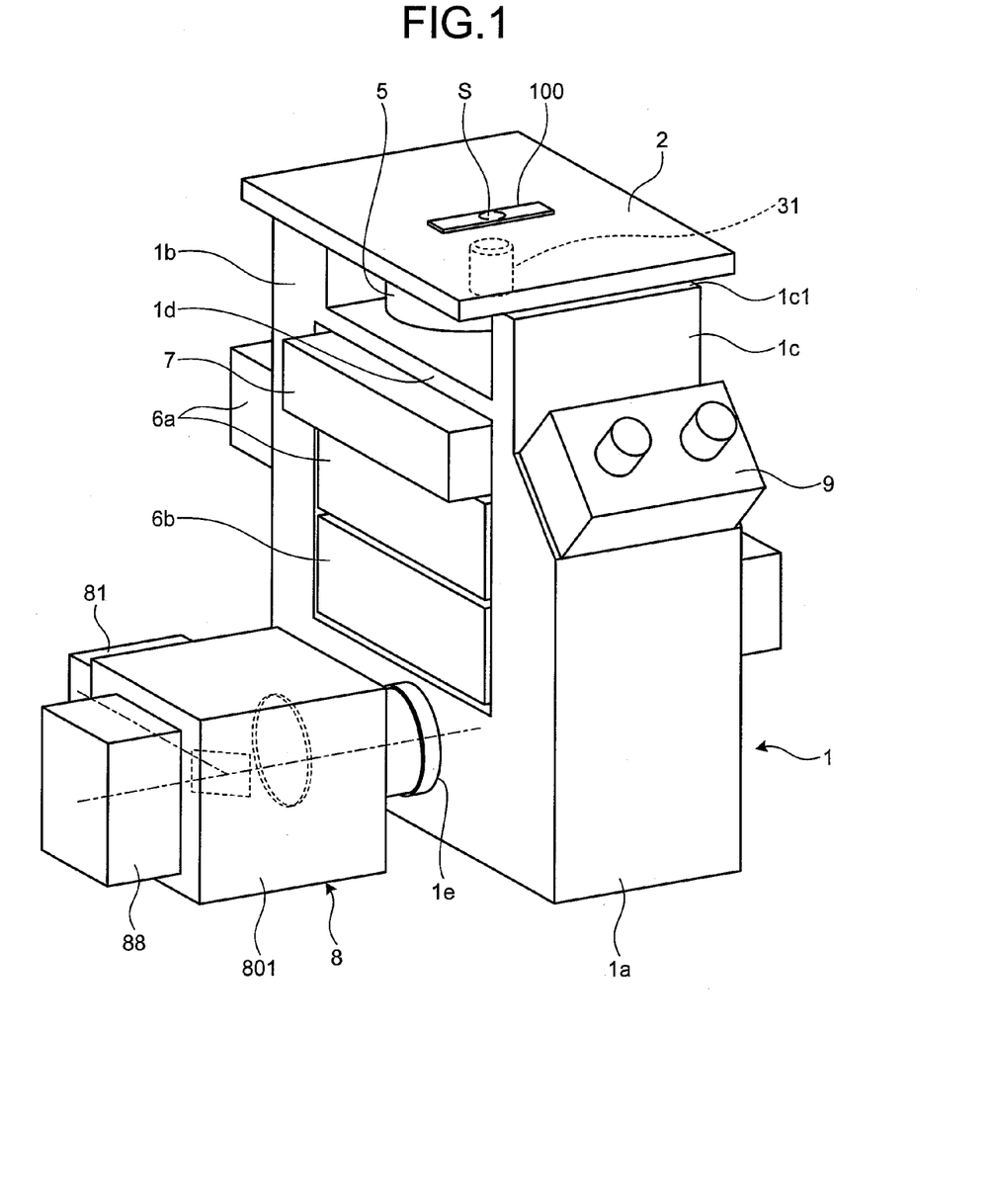
FIG. 1 is a schematic diagram of the whole configuration of an inverted microscope system according to some embodiments of the invention.
Figure 2:
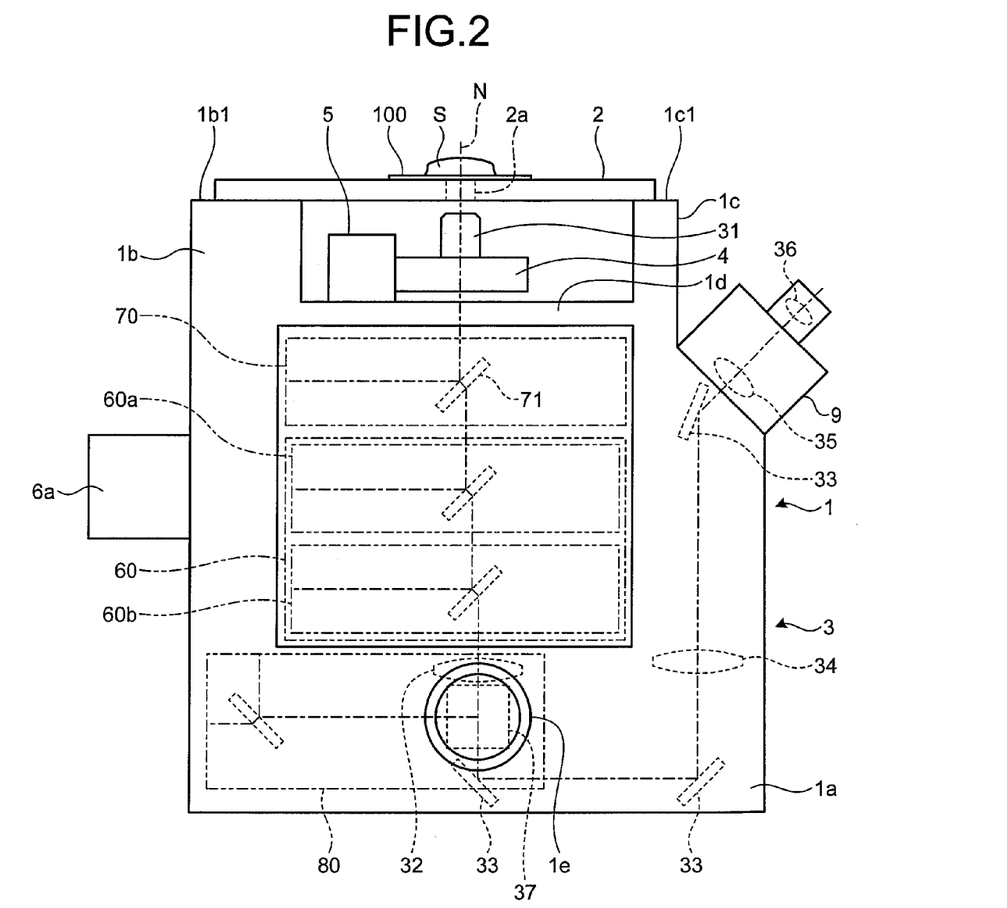
FIG. 2 is a side view of the internal configuration of the inverted microscope system according to some embodiments of the invention.

First, an inverted microscope system according to some embodiments of the invention will be described with reference to the drawings. FIG. 1 is a schematic diagram of the whole configuration of the inverted microscope system according to some embodiments. FIG. 2 is a side view of the internal configuration of the inverted microscope system illustrated in FIG. 1.

The inverted microscope system is configured to observe a specimen S that is to be observed from below the specimen S, and includes a microscope body 1 (main body), a stage 2 supported with the microscope body 1, and an observation optical system 3 configured to observe the specimen S placed on the stage 2 from underneath. Note that the inverted microscope system drives under the control by a control unit (not illustrated) that controls the whole of the inverted microscope system.

The microscope body 1 has a box shape, and includes a base 1a extending longitudinally, a rear wall 1b extending upward from the rear edge of the base 1a, a front wall 1c extending upward from the front edge of the base 1a, and a beam 1d connecting the upper portion of the rear wall 1b and the upper portion of the front wall 1c. Furthermore, an attachment area to which an objective lens 31 is attached is defined at the upper area of the microscope body 1.

An upper surface 1b1 of the rear wall 1b and an upper surface 1c1 of the front wall 1c form a plane extending horizontally. The stage 2 is attached and supported across the upper surface 1b1 of the rear wall 1b and the upper surface 1c1 of the front wall 1c.

The stage 2 has a flat board shape on each of the upper surface and the lower surface so as to place a specimen on the upper surface. An opening (opening hole) 2a of which size is not large enough such that the specimen S falls is provided almost at the center of the stage 2 so as to pass an excitation light or an observation light from the specimen S.

A revolver 4 (objective lens holding unit) and a focusing device 5 are attached to the upper surface of the beam 1d defined as the attachment area. The revolver 4 is rotatable and capable of moving up and down such that a plurality of the objective lenses 31 at different magnifications can be attached to the revolver 4. Then, one of the objective lenses 31 attached to the revolver 4 is placed on the optical axis. The focusing device 5 is configured to cause the objective lens 31 to focus on the specimen S. Operating the focusing device 5 moves the revolver 4 up and down. This causes the objective lens 31 attached to the revolver 4 to focus on the specimen S.

On the other hand, an attachment area to which a total reflection illumination optical unit 6a, a total reflection illuminating observation optical unit 6b, and an automatic focus optical unit 7 are attached is defined at the lower area of the beam 1d. Engaging grooves, for example, that are longitudinally paired are formed at the internal side of the rear wall 1b and the internal inside the front wall 1c that are defined as the attachment area. The total reflection illumination optical unit 6a, the total reflection illuminating observation optical unit 6b, and the automatic focus optical unit 7 can be detachably attached using the engaging grooves. A confocal unit 8 including a disk scanning confocal optical system 80 is detachably connected to the base 1a.

A total internal reflection illumination optical system 60a is formed inside the total reflection illumination optical unit 6a. A total internal reflection illuminating observation optical system 60b is formed inside the total reflection illuminating observation optical unit 6b. A total internal reflection illuminating and observation optical system 60 includes the total internal reflection illumination optical system 60a and the total internal reflection illuminating observation optical system 60b.

The total internal reflection illuminating and observation optical system 60 totally reflects illumination light from the interface of glass 100 on which the specimen S is placed so as to illuminate only the specimen very near the glass interface with an evanescent wave generated by the total reflect illumination. This enables the observation of the generated fluorescence.

An automatic focus optical system 70 is formed inside the automatic focus optical unit 7. The automatic focus optical system 70 is not for observing the specimen S and is for automatically performing an operation for focusing on the specimen S that the speculum examiner performs. The automatic focus optical system 70 includes, for example, an automatic focus light source, a detector for obtaining a focus signal, and various optical components (not illustrated). The automatic focus optical system 70 emits the light from the automatic focus light source in the direction to the specimen S through a dichroic mirror 71 and detects the return light so as to control and drive the focusing device 5 using the obtained detection signal and under the control by the control unit. This automatically performs an operation for focusing on the specimen S.

As illustrated in FIG. 2, the observation optical system 3 enables the observation of a specimen, and is provided across the microscope body 1 and a binocular 9 attached to the microscope body 1. In addition to the objective lenses 31, the observation optical system 3 includes a tube lens 32, a mirror 33, a relay lens 34, a tube lens 35, and an eyepiece 36.

The tube lens 32, the mirror 33, and the relay lens 34 are attached to the inside of the microscope body 1. Thus, the observation light that has passed through the objective lens 31 to become collimated light rays forms an image by passing through the tube lens 32 and enters the binocular 9 through the mirror 33 and the relay lens 34.

The tube lens 35 is attached to the inside of the binocular 9 and the eyepiece 36 is attached on the binocular 9. This causes the observation light that has entered from the microscope body 1 to form an image by passing through the tube lens 35. Looking through the eyepiece 36 can observe the image.

An optical path splitting member 37 for splitting an optical path is provided between the tube lens 32 and the mirror 33 (the relay lens 34). For example, a beam splitter or half mirror having a division ratio of the reflection to the transmission that is one to one is used as the optical path splitting member 37. The optical path splitting member 37 divides light into an optical path transmitted through the optical path splitting member 37 in the direction of an optical axis N (downward on the drawing paper) and led to the binocular 9, and an optical path reflected in a direction perpendicular to the drawing paper from the optical axis N of the objective lens 31 with the optical path splitting member 37. The optical path reflected in a direction perpendicular to the drawing paper from the optical axis N of the objective lens 31 enters an external port 1e connected to an image device including a CCD image sensor or a CMOS image sensor.

The confocal unit 8 is connected to the external port 1e. The disk scanning confocal optical system 80 is formed at the inside of the confocal unit 8. The disk scanning confocal optical system 80 includes a disk provided with a confocal opening such as a slit or a pinhole at a position conjugate to an irradiation surface of the illumination light on the specimen S (the focus position of the objective lens 31) so as to spin the disk at a high speed. This can observe only the fluorescence from the irradiation surface in real time.

Figure 3:
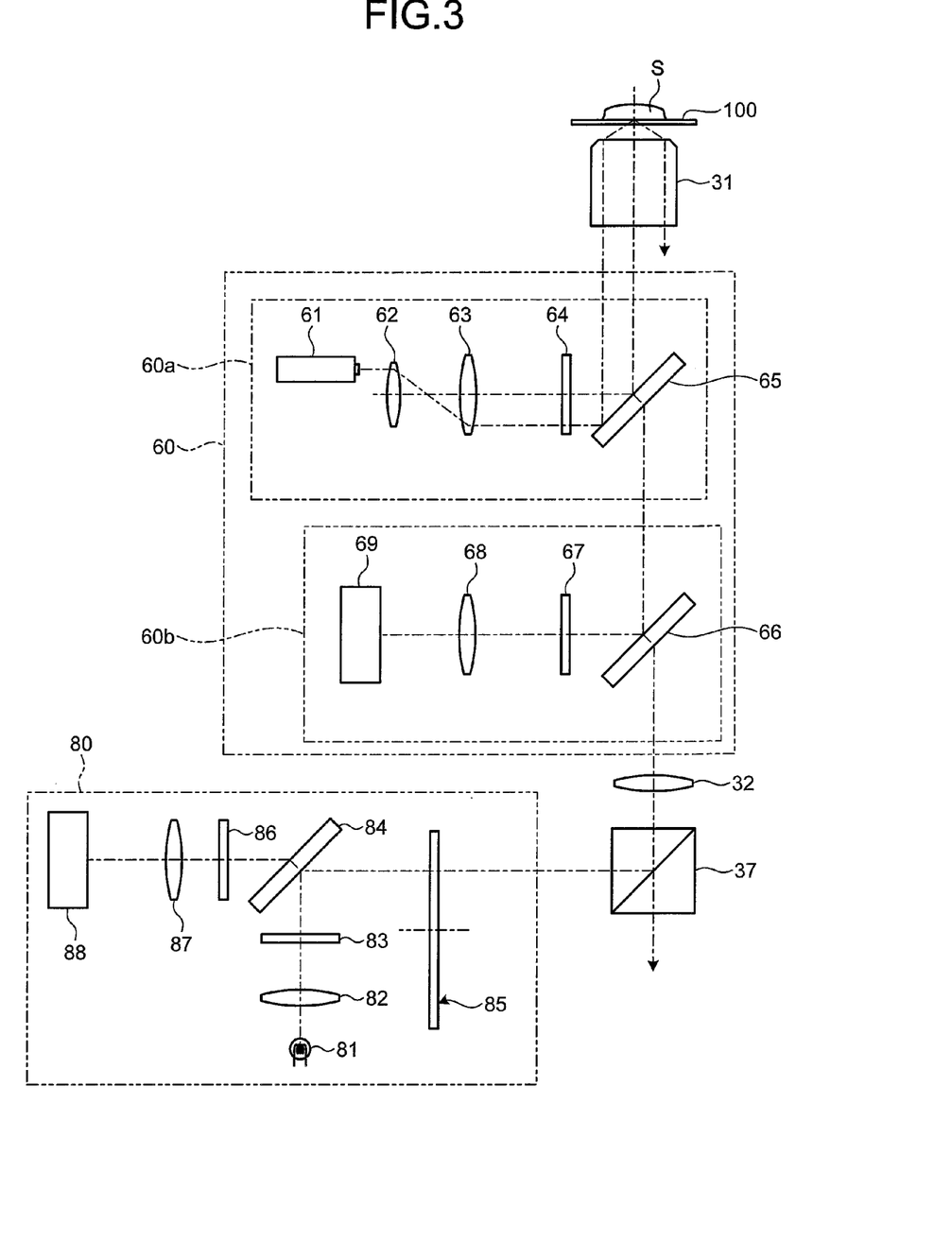
FIG. 3 is a schematic view of the configuration of the main components of the inverted microscope system according to some embodiments of the invention.

Next, the total internal reflection illuminating and observation optical system 60 and the disk scanning confocal optical system 80 will be described with reference to the drawings. FIG. 3 is a schematic diagram of the configuration of the main components of the inverted microscope system according to some embodiments of the invention. FIG. 3 illustrates the configuration of the total internal reflection illuminating and observation optical system 60 and the disk scanning confocal optical system 80.

The total internal reflection illuminating and observation optical system 60 includes the total internal reflection illumination optical system 60a and the total internal reflection illuminating observation optical system 60b. The total internal reflection illumination optical system 60a includes a laser light source 61, a lenses 62 and 63, an excitation filter 64, and a dichroic mirror 65. The laser light source 61 emits laser light including light of a specified wavelength.

The excitation filter 64 transmits light corresponding to the wavelength of the excitation light for exciting the fluorescent pigment labeling the specimen S with the fluorescence among the laser light from the laser light source 61.

The dichroic mirror 65 selectively reflects or transmits light of a specified wavelength. The dichroic mirror 65, for example, reflects light corresponding to the wavelength of the excitation light for exciting the fluorescent pigment labeling the specimen S with the fluorescence and transmits light of a wavelength other than the wavelength.

The total internal reflection illuminating observation optical system 60b includes a dichroic mirror 66, an absorption filter 67, a tube lens 68, and an imaging device 69.

The dichroic mirror 66 selectively reflects or transmits light of a specified wavelength. The dichroic mirror 66, for example, reflects light corresponding to the wavelength of the observation light from the fluorescent pigment labeling the specimen S with the fluorescence and transmits light of another wavelength.

The absorption filter 67 selectively transmits light corresponding to the wavelength of the observation light (fluorescence) from the fluorescent pigment labeling the specimen S with the fluorescence and absorbs light of another wavelength.

The imaging device 69 includes a CCD image sensor or a CMOS image sensor to receive the observation light with which the tube lens 68 has formed an image and generate an image signal.

Figure 4:
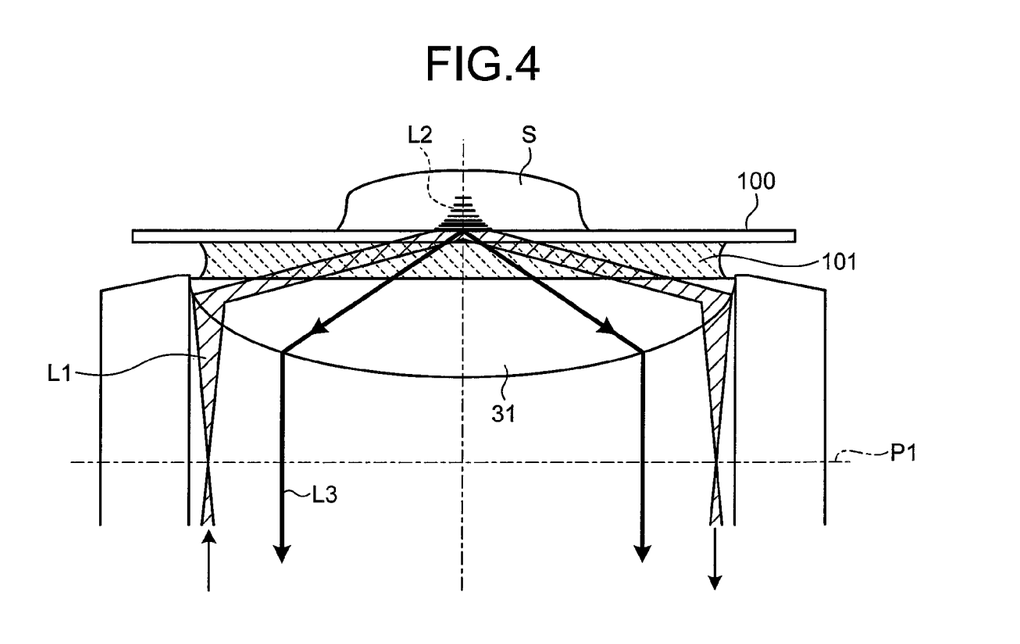
FIG. 4 is a diagram for describing a total internal reflection fluorescence microscopy optical system in the inverted microscope system according to some embodiments of the invention.

FIG. 4 is a diagram for describing the total internal reflection illuminating and observation optical system 60 in the inverted microscope system according to some embodiments.

FIG. 4 illustrates the neighborhood of the objective lens 31. Laser light L1 that is emitted from the laser light source 61 and is reflected from the dichroic mirror 65 enters the outer edge of the objective lens 31 and is refracted on the outer edge to enter the glass 100 at an angle at which the laser light L1 is totally reflected from the boundary of the glass 100 and the specimen S. At that time, collecting the laser light L1 at a rear focus position P1 of the objective lens 31 causes the laser light L1 to enter the glass 100 as collimated light. The laser light L1 totally reflected from the boundary of the glass 100 and the specimen S enters the outer edge of the objective lens 31 again. Note that the space between the objective lens 31 and the glass 100 is filled with immersion oil 101.

When the laser light L1 is totally reflected from the boundary between the glass 100 and the specimen S, an evanescent wave L2 exudes in a range of several hundred nm on the specimen S side from the glass 100. The exuding evanescent wave L2 can locally illuminate only the specimen S near the interface of the glass 100. A fluorescence L3 excited and generated by the evanescent wave L2 passes through the objective lens 31 and the dichroic mirror 65 and is reflected from the dichroic mirror 66 so as to be led to the imaging device 69. As described above, there is not an unnecessary illumination light other than the evanescent wave in the total internal reflection illuminating and observation optical system 60. This can obtain an image with very good contrast. This can also do little damage to the specimen S and thus can prevent the photobleaching of the fluorescent pigment as much as possible.

Figure 5:
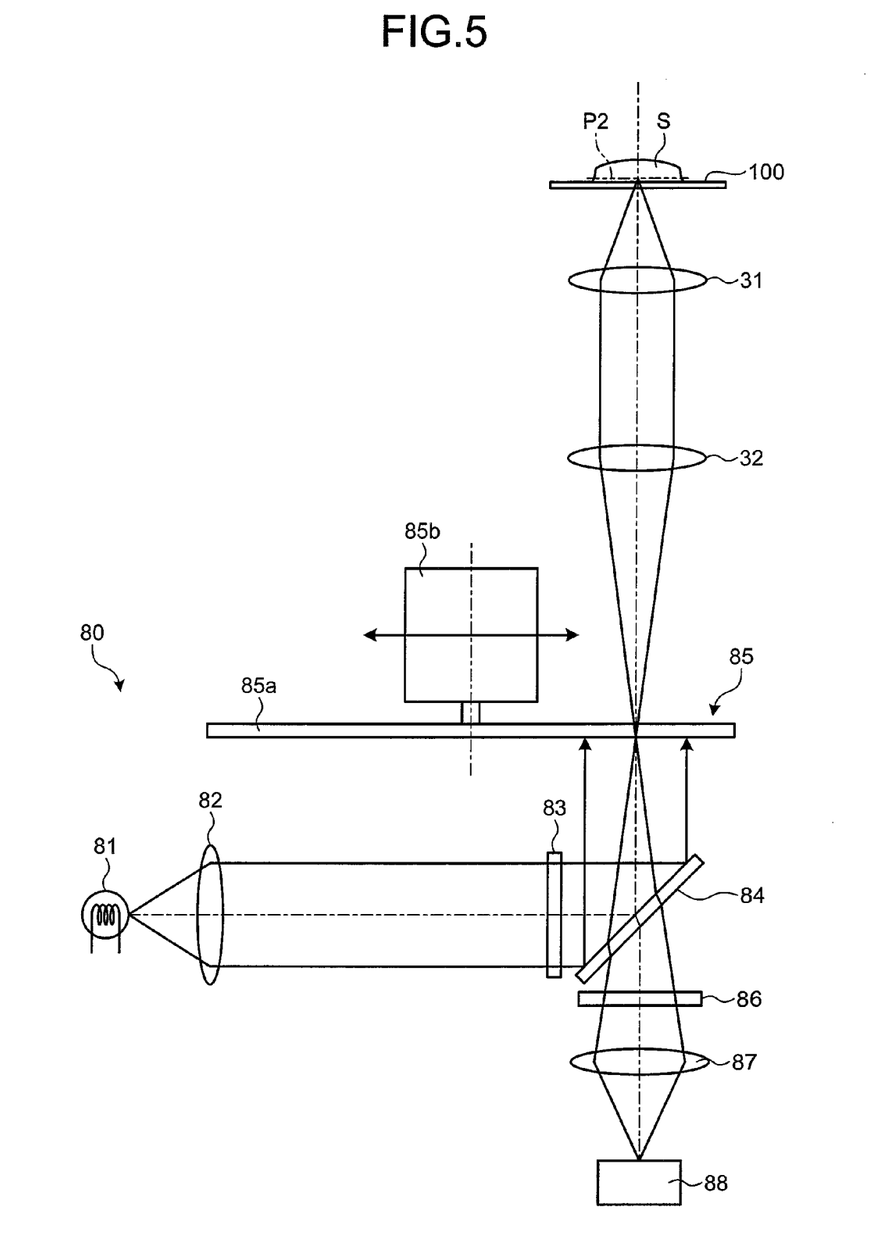
FIG. 5 is a schematic diagram of the configuration of the main components of the inverted microscope system according to some embodiments of the invention.

FIG. 5 is a schematic diagram of the configuration of the main components of the inverted microscope system according to some embodiments. FIG. 5 illustrates the configuration of the disk scanning confocal optical system 80. Note that, for description, the optical path splitting member 37 is omitted. The disk scanning confocal optical system 80 includes a light source 81, a lens 82, an excitation filter 83, a dichroic mirror 84, a rotary disk 85, an absorption filter 86, a tube lens 87, and an imaging device 88. The disk scanning confocal optical system 80 and the objective lens 31 are disposed on opposite sides of the tube lens 32, and the disk scanning confocal optical system 80 is placed beyond the tube lens 32 in the observation optical system 3.

For example, a mercury light source is used as the light source 81, and emits a white light.

The excitation filter 83 transmits light corresponding to the wavelength of the excitation light for exciting the luminescent material that the specimen S holds among the white light from the light source 81.

The dichroic mirror 84 selectively reflects or transmits light of a specified wavelength. The dichroic mirror 84, for example, transmits light corresponding to the wavelength of the observation light from the fluorescent pigment labeling the specimen S with the fluorescence and reflects light of another wavelength.

The rotary disk 85 includes a disk portion 85a having a board shape and provided with a plurality of confocal openings such as slits or pinholes, and a driving portion 85b that spins the disk portion 85a using a shaft perpendicular to the principal surface of the disk portion 85a as the central axis. The rotary disk 85 is provided such that the confocal opening of the disk portion 85a is located at an intermediate image position (the focus position of the tube lens 32) substantially conjugate to the irradiation surface of the illumination light on the specimen S (the focus position of the objective lens 31). The driving portion 85b spins the disk portion 85a at a constant speed. A light transmissive material such as glass is used as the disk material for the disk portion 85a. Patters of the confocal openings are formed on the surface of the disk by a metal film coating, for example, with chrome. For example, a motor that spins the disk portion 85*a* around the central axis passing through the center of the principal surface of the disk portion 85*a* is used as the driving portion 85*b*.

The absorption filter 86 selectively transmits light corresponding to the wavelength of the observation light (fluorescence) from the fluorescent pigment labeling the specimen S with the fluorescence and absorbs light of another wavelength.

The imaging device 88 includes a CCD image sensor or a CMOS image sensor to receive the observation light with which the tube lens 87 has formed an image and generate an image signal.

Subsequently, the irradiation of the illumination light and the obtaining of the observation light in the disk scanning confocal optical system 80 will be described. The illumination light emitted from the light source 81 passes through the lens 82 and the excitation filter 83 and becomes, illumination light of a specified wavelength. Then, the illumination light is reflected from the dichroic mirror 84 and enters the rotary disk 85.

The disk portion 85*a* of the rotary disk 85 spins at a constant speed by the driving of the driving portion 85*b*. The illumination light that has passed through the confocal openings on the disk portion 85*a* is projected and irradiated as a plurality of confocal opening images on the specimen S (illumination position P2) on the glass 100 through the tube lens 32 and the objective lens 31.

The observation light (fluorescence) emitted from the fluorescent pigment labeling, with the fluorescence, the specimen S excited by the irradiation of the illumination light similarly passes through the objective lens 31, the tube lens 32, and the confocal openings of the rotary disk 85 and is transmitted through the dichroic mirror 84. After that, the light transmitted through the dichroic mirror 84 is collected on the imaging device 88 with the tube lens 87 through the absorption filter 86. In the disk scanning confocal optical system 80, the illumination light and the observation light pass through a part of the optical path of the total internal reflection illuminating and observation optical system 60.

As described above, the installation position of the disk portion 85*a* and the illumination position P2 (=the focus position of the objective lens) are conjugate to each other. Thus, only the light from the specimen surface at the illumination position P2 observed with the objective lens 31 is collected on the imaging device 88. This can provide a confocal image with a high sectioning effect in the optical axis in real time.

The generated fluorescence hardly decays even after passing through the rotary disk 85 although the illumination light decays to about several percent of the light quantity of the illumination light emitted from the light source 81 by passing through the rotary disk 85. This can also do little damage to the specimen S and thus can prevent the photobleaching of the fluorescent pigment as much as possible.

Figure 6:
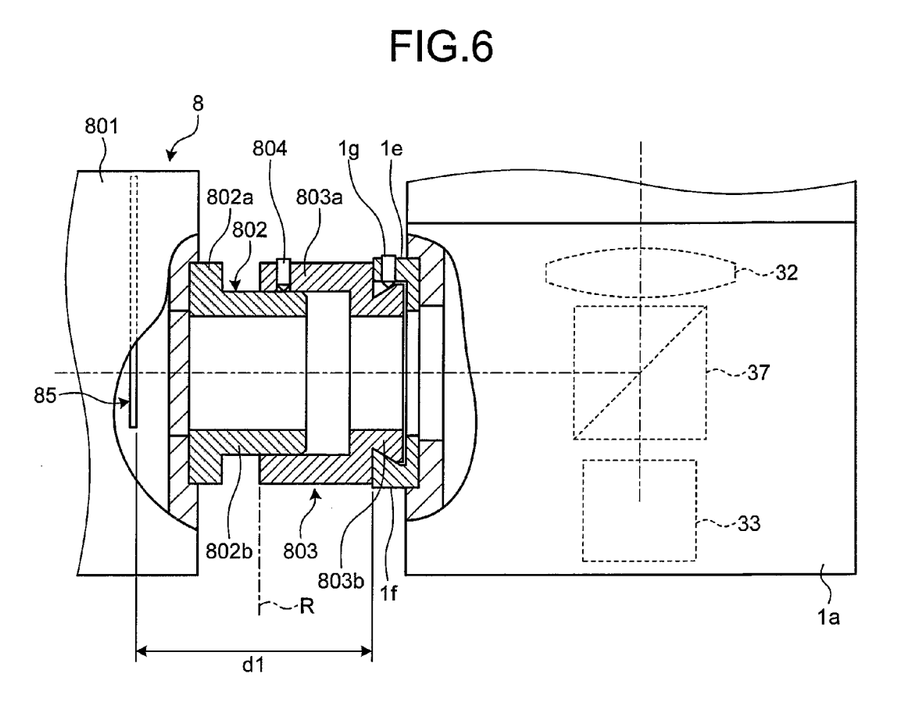
FIG. 6 is a schematic partial cross-sectional diagram of the configuration of the main components of the inverted microscope system according to some embodiments of the invention.

Subsequently, the connection between the external port 1*e* and the confocal unit 8 will be described with reference to the drawing. FIG. 6 is a schematic partial cross-sectional diagram of the configuration of the main components of the inverted microscope system according to some embodiments. A connecting unit 1*f* configured to connect the external port 1*e* to the confocal unit 8 is formed at the external port 1*e*.

The connecting unit 1*f* is a concave circular dovetail and includes an opening on the bottom of the concave. The connecting unit 1*f* is placed such that the light entering the optical path splitting member 37 or the light deflected with the optical path splitting member 37 passes through the central axis of the opening.

The confocal unit 8 includes a housing 801 including the disk scanning confocal optical system 80 therein, and an opening having the central axis corresponding to the optical axis of the light emitted from the rotary disk 85 or entering the rotary disk 85. The confocal unit 8 further includes a protrusion 802 projecting from the side surface of the housing 801, and a coupling unit 803 to which each of the protrusion 802 and the connecting unit 1*f* is detachably provided.

The protrusion 802 includes a base 802*a* coupled to the housing 801, and a cylindrical portion 802*b* projecting from the base 802*a* and having a cylindrical shape.

The coupling unit 803 includes a tubular portion 803*a* having an internal diameter almost the same as the external diameter of the cylindrical portion 802*b*, and an adapter 803*b* provided on an end of the tubular portion 803*a* in the central axial direction and having a convex circular dovetail shape capable of fitting with the circular dovetail of the connecting unit 1*f*.

In that case, the cylindrical portion 802*b* is inserted in the tubular portion 803*a* and a fixing screw 804 fixes the relative position of the cylindrical portion 802*b* and the tubular portion 803*a* through a through-hole formed on the side surface of the tubular portion 803*a* in the coupling unit 803. The circular dovetail shapes of the connecting unit 1*f* and the adapter 803*b* are fitted with each other while a fitting screw 1*g* fixes the relative position of the connecting unit 1*f* and the adapter 803*b* through a through-hole formed on the side surface of the connecting unit 1*f*.

The cylindrical portion 802*b* is marked with scales indicating the relative position to the tubular portion 803*a*. Thus, adjusting the position with the scales can determine the relative position to the tubular portion 803*a*. On the assumption that the position of the cylindrical portion 802*b* when the install position of the disk portion 85*a* of the rotary disk 85 is conjugate to the illumination position P2 (=the focus position of the objective lens) is a reference position R, and a distance d1 is defined as a distance from the edge surface of the disk portion 85*a* to the edge surface of the connecting unit 1*f* at that time, adjusting the position of the cylindrical portion 802*b* to the position of the scale corresponding to the distance d1 can define the reference position R. As described above, loosing the fixing screw 804 can arbitrarily change the position of the cylindrical portion 802*b* relative to the tubular portion 803*a* and can return the changed position to the reference position R. Note that, instead of the scales, spacers having different thicknesses can also be used to adjust the position. In such a case, using a spacer having a thickness corresponding to the distance d1 positions the cylindrical portion 802*b* on the reference position R.

Figure 7:
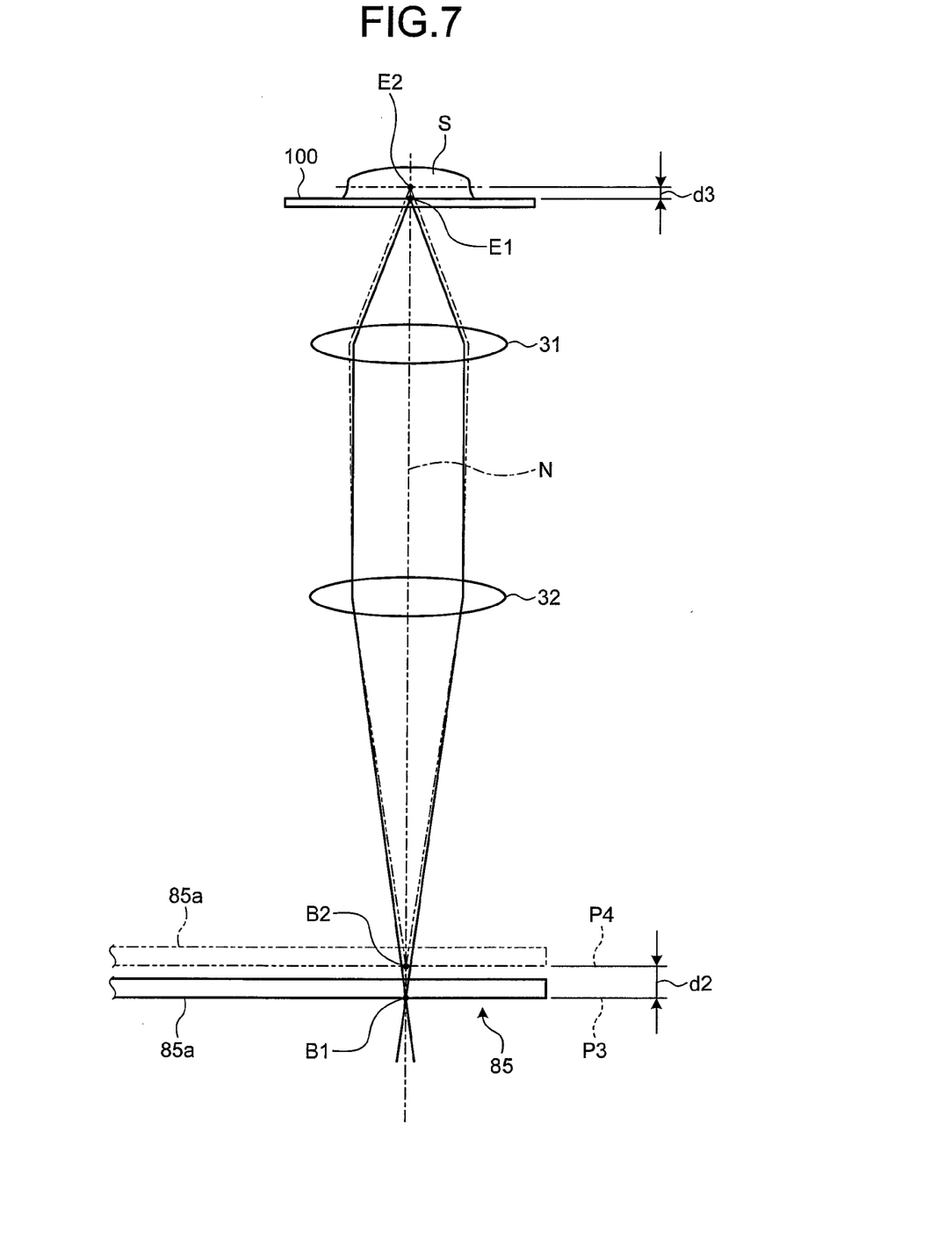
FIG. 7 is a schematic diagram of the configuration of the main components of the inverted microscope system according to some embodiments of the invention.

FIG. 7 is a schematic diagram of the configuration of the main components of the inverted microscope system according to some embodiments. FIG. 7 is a diagram for describing the variation of the illumination position with the disk scanning confocal optical system 80. Moving the cylindrical portion 802*b* to the tubular portion 803*a* moves an edge surface position P3 of the disk portion 85*a* to an edge surface position P4 along the optical path. On the assumption that this movement slides a position B1 of the confocal opening to a position B2, the projection position of the confocal opening image projected on the focus position of the objective lens 31 is also slid from a projection position E1 to a projection position E2 (the alternate long and two short dashes line in FIG. 7).

On the assumption that the sliding amount with the cylindrical portion 802*b* (the amount of movement of the disk portion 85*a*) is d2 and the slid amount of the conjugate position on the objective lens 31 side is d3, the slid amount d3 satisfies the relationship d3=d2/(the square of the objective lens magnification). For example, on the assumption that the movement amount d2 of the disk portion 85*a* is 2 mm and the objective lens 31 is at 60-fold magnification, the slid amount d3 of the conjugate position on the objective lens 31 side is about 550 nm. Thus, a confocal image is provided on the side that is about 550 nm rearward from the focus position of the objective lens 31 (=the specimen surface) that is the original conjugate position. The operation can change the observation position in the disk scanning confocal optical system 80.

In that case, the sliding amount d2 differs from the slid amount d3. Thus, the distance from the projection position E1 to the position B1 of the confocal opening differs from the distance from the projection position E2 to the position B2 of the confocal opening. In other words, the movement of the disk portion 85*a* changes the relative distance between the focus position of the objective lens 31 and the position substantially conjugate to the focus position.

According to some embodiments, changing the relative position of the tube lens 32 and the disk portion 85*a* of the disk scanning confocal optical system 80 changes the relative distance between the focus position of the objective lens 31 and the position substantially conjugate to the focus position. This changes the observation position in the disk scanning confocal optical system 80.

According to some embodiments, the disk scanning confocal optical system 80 includes the optical path shared with the total internal reflection illuminating and observation optical system 60 and is placed on the optical path below the tube lens 32 in the observation optical system 3. This sufficiently secures a working space just above the specimen and thus can provide an inverted microscope system have a low influence on the balance of gravity center of the whole system. This enables the observation in which a working space is secured and a low gravity center of the system reduces the influence of the vibration.

According to some embodiments, the total internal reflection illuminating and observation optical system 60 shares a single objective lens 31 with the disk scanning confocal optical system 80. This can provide an inverted microscope system at a low cost.

Note that, although a beam splitter or half mirror having a division ratio of the reflection to the transmission that is one to one is used as the optical device (optical path splitting member) configured to switch the optical paths in some embodiments, a dichroic mirror or beam splitter having a division ratio of the reflection to the transmission, for example, by a coating with a dielectric multi-layer, or a right angle prism or mirror having only a reflective optical path can be used.

Furthermore, although a single optical path splitting member 37 is provided in the microscope body 1 in some embodiments, a plurality of optical path splitting members 37 having different division ratios of the reflection to the transmission can be provided. For example, in addition to the beam splitter, a plurality of optical path splitting members such as right angle prisms (with only a reflective optical path) for attaching importance to the confocal observation side or cylindrical prisms (with only a transmissive optical path) for attaching importance to the visual observation side can be provided so as to appropriately switch between the optical path splitting members depending on the observation method.

Furthermore, although moving the whole of the confocal unit 8 changes the position of the rotary disk 85 on the optical path in the embodiments described above, the invention is not limited to the embodiments. A method in which the positions of the rotary disk 85 and other associated components can separately be changed in the confocal unit 8 can be applied.

Figure 8:
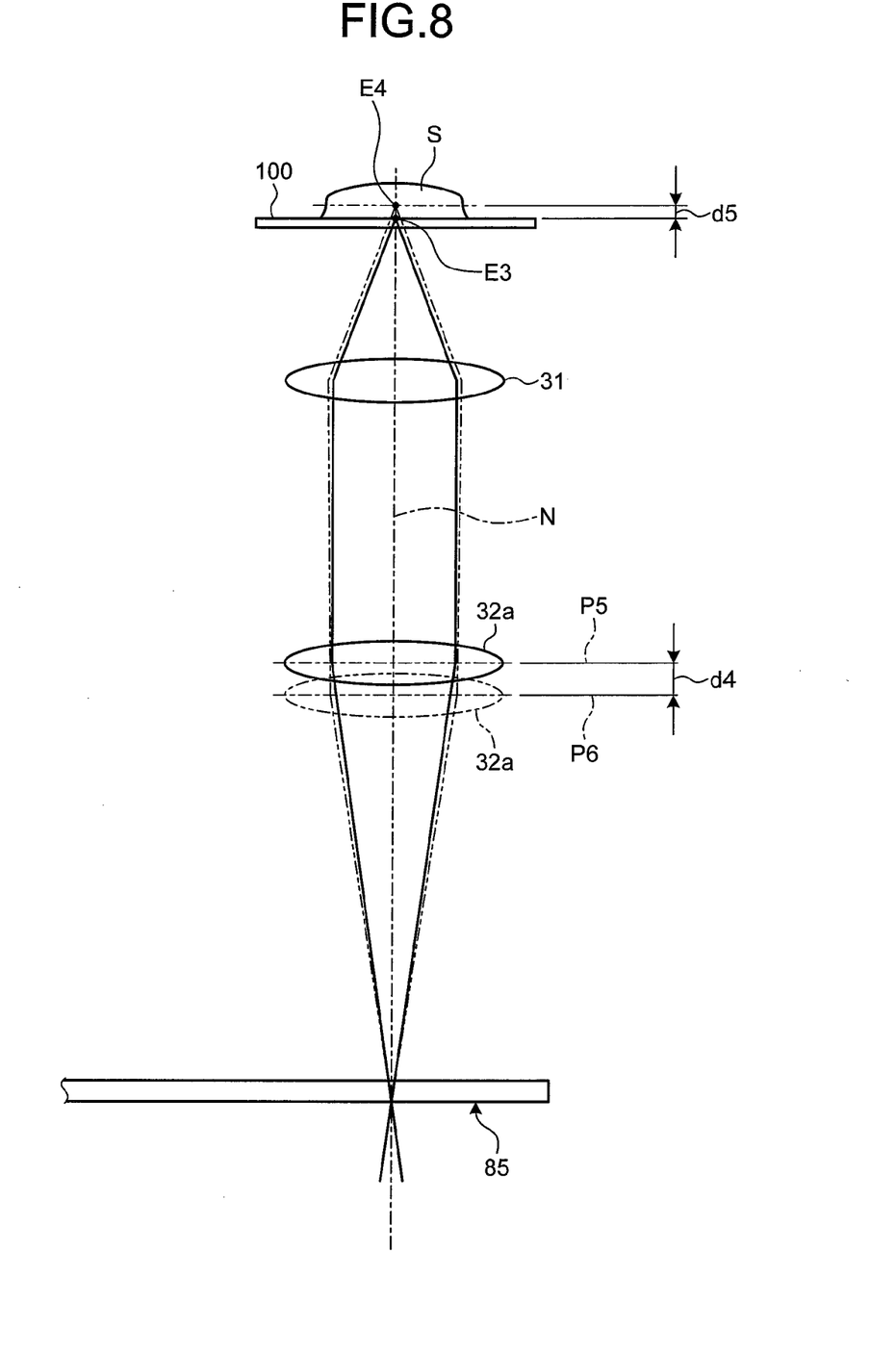
FIG. 8 is a schematic diagram of the configuration of the main components of an inverted microscope system according to an exemplary variation 1 of some embodiments of the invention.

FIG. 8 is a schematic diagram of the configuration of the main components of the inverted microscope system according to an exemplary variation 1 of some embodiments of the invention. FIG. 8 is a diagram for describing the variation of the observation position in the disk scanning confocal optical system 80. Changing the relative position of the microscope body 1 and the confocal unit 8 changes the observation position in the disk scanning confocal optical system 80 in the embodiment. However, moving a tube lens can change the observation position in the disk scanning confocal optical system 80 as in the exemplary variation 1.

A tube lens 32*a* is provided movably along an optical axis N of an objective lens 31 in the exemplary variation 1 illustrated in FIG. 8. Specifically, for example, a driving unit (not illustrated) moves the tube lens 32*a*, or a plurality of through-holes is provided so as to insert the tube lens into a through-hole corresponding to the observation position. This can change the observation position in a disk scanning confocal optical system 80. Similarly to the embodiment, the changed observation position can be returned to the original reference position, for example, using scales (not illustrated).

For example, on the assumption that the center of the tube lens 32*a* has moved along the optical axis N to a position P6 that is a distance d4 away from a position P5, the projection position of the confocal opening image projected on the focus position of the objective lens 31 is also slid from a projection position E3 to a projection position E4 (the alternate long and two short dashes line in FIG. 8).

On the assumption that the slid amount of the conjugate position on the objective lens 31 side (the distance between the projection position E3 and the projection position E4) is d5, the slid amount d5 satisfies the relationship d5=d4/(the square of the objective lens magnification). For example, on the assumption that the distance d4 that is the movement amount of the tube lens 32*a* is 2 mm and the objective lens 31 is at 60-fold magnification, the slid amount d5 of the conjugate position on the objective lens 31 side is about 550 nm. Thus, a confocal image is provided on the side that is about 550 nm rearward from the focus position of the objective lens 31 (=the specimen surface) that is the original conjugate position. The operation can change the observation position in the disk scanning confocal optical system 80.

In that case, the distance d4 differs from the slid amount d5. Thus, the distance from the projection position E3 to the confocal opening differs from the distance from the projection position E4 to the confocal opening. In other words, the movement of the tube lens 32*a* changes the relative distance between the focus position of the objective lens 31 and the position substantially conjugate to the focus position.

Figure 9:
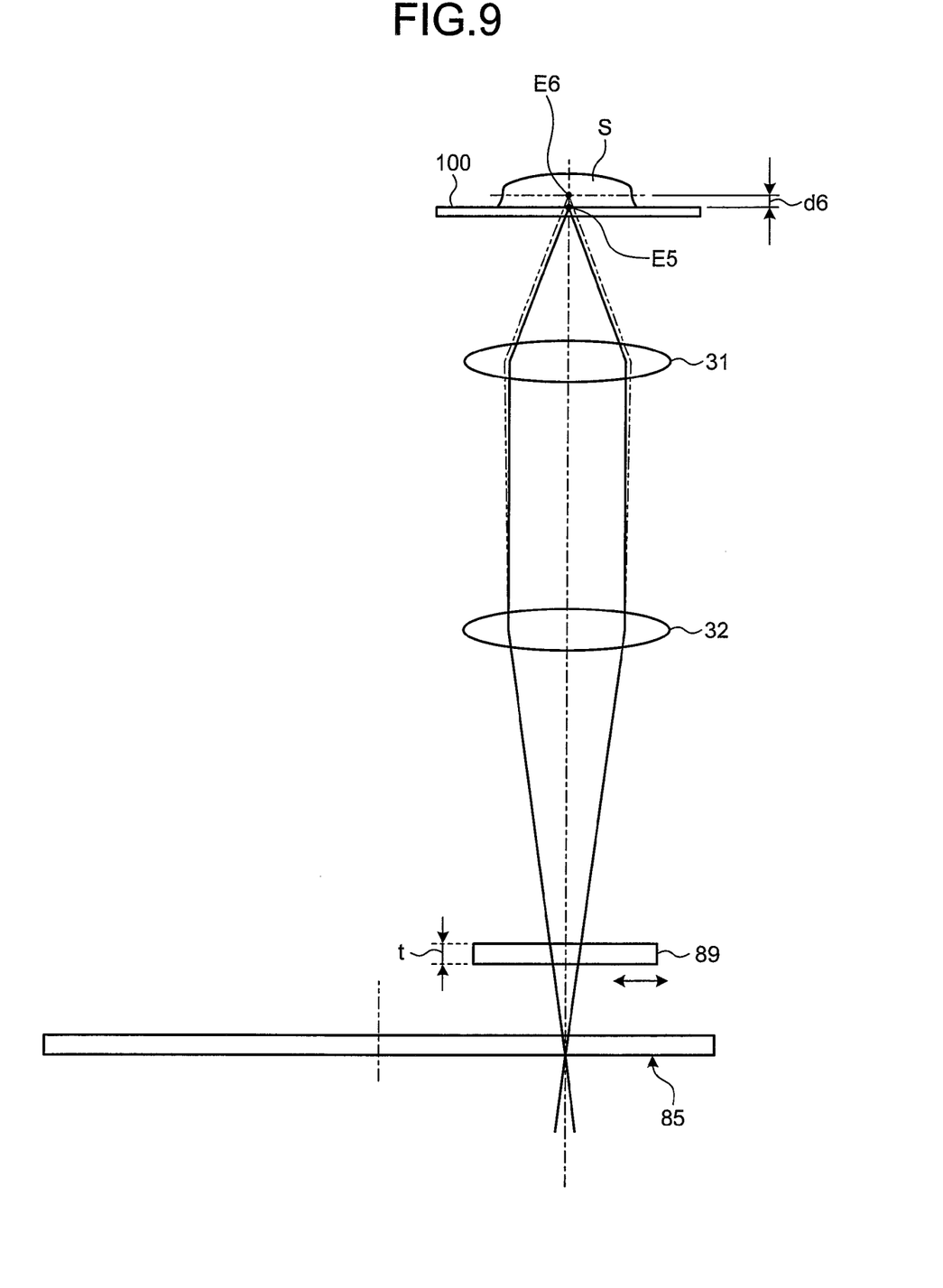
FIG. 9 is a schematic diagram of the configuration of the main components of an inverted microscope system according to an exemplary variation 2 of some embodiments of the invention.

FIG. 9 is a schematic diagram of the configuration of the main components of an inverted microscope system according to an exemplary variation 2 of some embodiments. FIG. 9 is a diagram for describing the variation of the observation position in a disk scanning confocal optical system 80. Changing the relative position of the microscope body 1 and the confocal unit 8 changes the observation position in the disk scanning confocal optical system 80 in the embodiment. However, a plane parallel glass (hereinafter, referred to as a glass board) can be placed between a tube lens 32 and a rotary disk 85 on the optical axis as in the exemplary variation 2. This can change the observation position in the disk scanning confocal optical system 80.

In the exemplary variation 2 illustrated in FIG. 9, a glass board 89 can be placed between the tube lens 32 and the rotary disk 85 on the optical axis such that a driving unit (not illustrated) can select the glass board 89. A plurality of glass boards 89 having different thicknesses is provided in the exemplary variation 2 such that one of the glass boards is selectively placed between the tube lens 32 and the rotary disk 85. The observation position in the disk scanning confocal optical system 80 can be changed in the optical axis direction depending on the thickness of the placed glass board. Similarly to the embodiments described above, displacing the glass board 89 can return to the original reference position.

For example, on the assumption that a glass board 89 having a refraction index n and a thickness t mm has been inserted, the projection position of the confocal opening image projected on the focus position of an objective lens 31 is also slid from a projection position E5 to a projection position E6 (see FIG. 9).

On the assumption that the slid amount of the conjugate position on the objective lens 31 side (the distance between the projection position E5 and the projection position E6) is d6, the slid amount d6 approximately satisfies the relationship $d6=t(1-1/n)/$(the square of the objective lens magnification). For example, on the assumption that the thickness t of the glass board is 3 mm, the refraction index n of the glass board is 1.5 and the objective lens 31 is at 60-fold magnification, the slid amount d6 of the conjugate position on the objective lens 31 side is about 280 nm. Thus, a confocal image is provided on the side that is about 280 nm rearward from the focus position of the objective lens 31 (=the specimen surface) that is the original conjugate position. The operation can change the observation position in the disk scanning confocal optical system 80. In that case, the refraction index of the glass board differs from the refraction index of the air. Thus, the distance from the projection position E5 to the confocal opening (without the glass board) differs from the air conversion distance from the projection position E6 to the confocal opening (the distance obtained by converting the thickness of the glass board to the distance in the air). In other words, inserting a glass board 89 having a different thickness changes the relative distance between the focus position of the objective lens 31 and the position substantially conjugate to the focus position.

Although the glass board 89 is inserted according to the exemplary variation 2, the invention is not limited to the exemplary variation 2. Any material having a sufficient permeability other than glass can be employed.

Instead of inserting the glass board 89 according to the exemplary variation 2, rotary disks having different glass thicknesses in the radial direction can be employed such that a driving unit (not illustrated) can arbitrarily change the position (change the thickness of the rotary disk placed on the optical path) during the confocal observation.

As described above, the inverted microscope system according to some embodiments can change the observation position in a disk scanning confocal optical system, and is useful in the observation in which a working space is secured and the influence of the vibration is reduced when an inverted microscope system with a total internal reflection fluorescence microscopy optical system and a disk scanning confocal optical system is used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inverted microscope system comprising:
   an objective lens holding unit that holds an objective lens configured to collect at least observation light from a specimen;
   a tube lens configured to form an image using the observation light collected by the objective lens;
   a total internal reflection fluorescence microscopy optical system provided between the objective lens and the tube lens and configured to observe the observation light from the specimen using a total reflection illumination; and
   a disk scanning confocal optical system including a rotary disk in which a confocal opening is formed, the confocal opening being placed at a position substantially conjugate to a focus position of the objective lens,
   wherein a relative distance between the focus position of the objective lens and the substantially conjugate position is changeable along an optical path of the observation light,
   wherein the disk scanning confocal optical system passes through a part of an optical path of the total internal reflection fluorescence microscopy optical system,
   wherein the disk scanning confocal optical system and the objective lens are disposed on opposite sides of the tube lens,
   wherein the inverted microscope system further comprises at least one optical path splitting member between the tube lens and the rotary disk, and
   wherein the disk scanning confocal optical system is removable from a main body that holds the objective lens holding unit and the tube lens.

2. The inverted microscope system according to claim 1, wherein the confocal opening in the rotary disk is placed at a focus position of the tube lens.

3. The inverted microscope system according to claim 2, wherein a movement of a position of the rotary disk along the optical path of the observation light changes the relative distance between the focus position of the objective lens and the substantially conjugate position.

4. The inverted microscope system according to claim 2, wherein a movement of a position of the tube lens along the optical path of the observation light changes the relative distance between the focus position of the objective lens and the substantially conjugate position.

5. The inverted microscope system according to claim 2, wherein selectively placing a plurality of permeable plane parallel boards having different thicknesses between the tube lens and the rotary disk on the optical path of the observation light changes the relative distance between the focus position of the objective lens and the substantially conjugate position.

* * * * *